US012758314B2

(12) United States Patent
Ma et al.

(10) Patent No.: US 12,758,314 B2
(45) Date of Patent: Oct. 13, 2026

(54) SYSTEMS AND METHODS FOR 3D DATA DRIVEN LASER ORIENTATION PLANNING

(71) Applicant: Duke University, Durham, NC (US)

(72) Inventors: Guangshen Ma, Durham, NC (US); Weston Ross, Durham, NC (US); Patrick Codd, Durham, NC (US)

(73) Assignee: Duke University, Durham, NC (US)

( * ) Notice: Subject to any disclaimer, the term of this patent is extended or adjusted under 35 U.S.C. 154(b) by 838 days.

(21) Appl. No.: 18/084,777

(22) Filed: Dec. 20, 2022

(65) Prior Publication Data

US 2023/0190379 A1 Jun. 22, 2023

Related U.S. Application Data

(60) Provisional application No. 63/291,507, filed on Dec. 20, 2021.

(51) Int. Cl.
*A61B 34/10* (2016.01)
*A61B 18/00* (2006.01)
(Continued)

(52) U.S. Cl.
CPC .............. *A61B 34/10* (2016.02); *A61B 18/20* (2013.01); *A61B 34/30* (2016.02); *A61B 90/361* (2016.02);
(Continued)

(58) Field of Classification Search
CPC ......... A61B 34/10; A61B 18/20; A61B 34/30; A61B 90/361; A61B 2018/00577;
(Continued)

(56) References Cited

U.S. PATENT DOCUMENTS 9,084,622 B2 7/2015 Rastegar et al.
9,498,295 B2 11/2016 Palanker
(Continued)

FOREIGN PATENT DOCUMENTS

WO WO-2018152538 A1 * 8/2018 ............. G16H 50/70

OTHER PUBLICATIONS

Ma, "Robotic Laser Orientation Planning with a 3D Data-driven Method", Jan. 5, 2022, arXiv (Year: 2022).*
(Continued)

*Primary Examiner* — Oneal R Mistry
*Assistant Examiner* — Justin Philip Cascais
(74) *Attorney, Agent, or Firm* — Casimir Jones, S.C.; Brian F. Bradley

(57) ABSTRACT

The present disclosure describes a method comprising ablating a substrate with a laser at an orientation to create a cavity in the substrate, scanning the cavity, and creating a three-dimensional surface for the cavity. The method further includes storing the three-dimensional surface in a dataset. The dataset includes a laser projected distance as an independent variable and a depth of cut as a dependent variable. The method further includes fitting parameters of a gaussian-based model for the laser and the substrate based on the dataset. The present disclosure also describes a method providing a pre-ablation surface, labeling a three-dimensional obstacle boundary that separates material to be remove by a laser and material to remain, and determining an orientation of the laser that results in a predicted post-ablation surface that does not intersect the three-dimension obstacle boundary.

13 Claims, 11 Drawing Sheets

(51) Int. Cl.

| | |
|---|---|
| ***A61B 18/20*** | (2006.01) |
| ***A61B 34/30*** | (2016.01) |
| ***A61B 90/00*** | (2016.01) |
| ***G06T 7/13*** | (2017.01) |
| ***G06T 7/521*** | (2017.01) |
| ***G06T 7/70*** | (2017.01) |
| ***G06T 12/10*** | (2026.01) |
| ***G06T 17/00*** | (2006.01) |

(52) U.S. Cl.

CPC ................ *G06T 7/13* (2017.01); *G06T 7/521* (2017.01); *G06T 7/70* (2017.01); *G06T 12/10* (2026.01); *G06T 17/00* (2013.01); *A61B 2018/00577* (2013.01); *A61B 2034/104* (2016.02); *A61B 2034/105* (2016.02); *A61B 2034/107* (2016.02); *G06T 2200/08* (2013.01); *G06T 2207/10028* (2013.01); *G06T 2207/10081* (2013.01); *G06T 2207/10101* (2013.01); *G06T 2207/30004* (2013.01); *G06T 2210/41* (2013.01)

(58) Field of Classification Search

CPC ........ A61B 2034/104; A61B 2034/105; A61B 2034/107; A61B 2034/101; A61B 2090/3735; G06T 7/13; G06T 7/521; G06T 7/70; G06T 11/005; G06T 17/00; G06T 2200/08; G06T 2207/10028; G06T 2207/10081; G06T 2207/10101; G06T 2207/30004; G06T 2210/41

See application file for complete search history.

(56) References Cited

U.S. PATENT DOCUMENTS

| | | | | |
|---|---|---|---|---|
| 2016/0070436 A1* | 3/2016 | Thomas | ................ | G06T 7/0012 715/771 |
| 2021/0034798 A1* | 2/2021 | Bruneel | ................ | B23K 26/00 |
| 2022/0157044 A1* | 5/2022 | Schick | ................... | G01B 11/22 |

OTHER PUBLICATIONS

Vakharia, "Automated trajectory planning for laser interstitial thermal therapy in mesial temporal lobe epilepsy", 2018, Epilepsia, pp. 814-824 (Year: 2018).*
"Baerentzen, Robust generation of signed distance fields from triangle meshes, 2005, Fourth International Workshop on Volume Graphics" (Year: 2005).*
Acemoglu et al., Laser incision depth control in robot-assisted soft tissue microsurgery. Journal of Medical Robotics Research, 2017, vol. 2, No. 03, p. 1740006. 12 pages.
Bay et al., Real-time monitoring of incision profile during laser surgery using shock wave detection. J Biophotonics. Jan. 2015;8(1-2):102-11.
Burgner et al., Ex vivo accuracy evaluation for robot assisted laser bone ablation. Int J Med Robot. Dec. 2010;6(4):489-500.
Channa et al., Robotic Vitreoretinal Surgery. Retina. Jul. 2017;37(7):1220-1228.
Coleman et al., An interior trust region approach for nonlinear minimization subject to bounds. SIAM Journal on Optimization, 1996, vol. 6, No. 2, pp. 418-445.
Dolgui et al., Manipulator motion planning for high-speed robotic laser cutting. International Journal of Production Research, 2009, vol. 47, No. 20, pp. 5691-5715.
Draelos et al., Contactless optical coherence tomography of the eyes of freestanding individuals with a robotic scanner. Nat Biomed Eng. Jul. 2021;5(7):726-736.
Draelos et al., Real-time visualization and interaction with static and live optical coherence tomography volumes in immersive virtual reality. Biomed Opt Express. May 30, 2018;9(6):2825-2843.
Emprint SX Ablation Platform (Medtronic). https://www.medtronic.com/covidien/en-us/products/ablation-systems/emprint-sx-ablation-system.html. Retrieved from the internet Jun. 19, 2023. 4 pages.
Fang et al., Orientation planning of robot endeffector using augmented reality. The International Journal of Advanced Manufacturing Technology, 2012; 67(9-12): 2033-2049.
Felzenszwalb et al., Distance transforms of sampled functions. Theory of Computing, 2012, vol. 8, No. 1, pp. 415-428.
Fichera et al., Online estimation of laser incision depth for transoral microsurgery: approach and preliminary evaluation. Int J Med Robot. Mar. 2016;12(1):53-61.
Gonzalez et al., Digital image processing. Pearson. 2002. TOC only. 10 pages.
Guo. A simple algorithm for fitting a gaussian function [dsp tips and tricks. IEEE Signal Processing Magazine. 2011; 28(5): 134-137.
Ihler et al., OPhonLas: OCT-controlled laser ablatio for vocal fold phonation. Leibniz University Hannover Insitute of Mechatronic Systems Jan. 6, 2017. 5 pages.
Jivraj et al., Robotic laser osteotomy through penscriptive structured light visual servoing. Int J Comput Assist Radiol Surg. May 2019;14(5):809-818.
Kahrs et al., Planning and simulation of microsurgical laser bone ablation. Int J Comput Assist Radiol Surg. Mar. 2010;5(2):155-62.
Kahrs et al., Visual servoing of a laser ablation based cochleostomy. Medical Imaging 2008: Visualization, Image-Guided Procedures, and Modeling. 2008, vol. 6918, 69182C. 1-11.
Leung et al., Real-time guidance of thermal and ultrashort pulsed laser ablation in hard tissue using inline coherent imaging. Lasers Surg Med. Mar. 2012;44(3):249-56.
Liao et al., An integrated diagnosis and therapeutic system using intra-operative 5-aminolevulinic-acid-induced fluorescence guided robotic laser ablation for precision neurosurgery. Med Image Anal. Apr. 2012;16(3):754-66.
Ma et al., A novel laser scalpel system for computer-assisted laser surgery. In 2019 International Conference on Robotics and Automation (ICRA) May 20, 2019. pp. 386-392.
Ma et al., Characterization of photoablation versus incidence angle in soft tissue laser surgery: an experimental phantom study. In Optical Interactions with Tissue and Cells XXXI Feb. 20, 2020 (vol. 11238, p. 112380G). 13 pages.
Ma et al., Robotic Laser Orientation Planning with a 3D Data-driven Method. arXiv preprint arXiv:2201.01401. Jan. 5, 2022. 9 pages.
Ma et al., StereoCNC: A Stereovision-guided Robotic Laser System. Rep U S. Sep.-Oct. 2021;2021:540-547.
Modeling and Control of Laser-Tissue Interactions. Project by Biomedical Robotics Lab at Italian Institute of Technology. https://advr.iit.it/laser-tissue-interactions-modeling-and-robotic-control. Retrieved from the internet Jun. 19, 2023. 5 pages.
Nocedal et al., Numerical Optimization. Springer Science & Business Media, 2006. TOC only. 16 pages.
OPhonLas: OCT-controlled Laser Ablation for Vocal Fold Phonation (project by Institute of Mechatronic Systems at Leibniz University Hannover). https://www.imes.uni-hannover.de/en/research/research-group-medical-technology-image-processing/research-projects/projects/ophonlas-oct-controlled-laser-ablation-for-vocal-fold-phonation/. Retrieved from the internet Jun. 19, 2023. 5 pages.
Penza et al., Hybrid visual servoing for autonomous robotic laser tattoo removal. 2019 IEEE/RSJ International Conference on Intelligent Robots and Systems (IROS). IEEE, 2019, pp. 4461-4466.
Radiofrequency Ablation Performance Platform (Stryker Corporation). https://www.stryker.com/us/en/portfolios/medical-surgical-equipment/image-guided-therapies/radiofrequency-neurotomy.html. Retrieved from the internet Jun. 19, 2023. 2 pages.
Ross et al., Automating neurosurgical tumor resection surgery: Volumetric laser ablation of cadaveric porcine brain with integrated surface mapping,. Lasers in Surgery and Medicine, vol. 0, No. 0. [Online]. Available: https://onlinelibrary.wiley.com/doi/abs/10.1002/lsm.23000. 2018; 1-8.
Ross et al., Optimized path planning for soft tissue resection via laser vaporization. Clinical and Translational Neurophotonics 2018, vol. 10480, SPIE, 2018. 8 pages.

(56) References Cited

OTHER PUBLICATIONS

Schoob et al., Tissue surface information for intraoperative incision planning and focus adjustment in laser surgery. Int J Comput Assist Radiol Surg. Feb. 2014;10(2):171-81.

Schulman et al., Motion planning with sequential convex optimization and convex collision checking. The International Journal of Robotics Research, 2014, vol. 33, No. 9, pp. 1251-1270.

Stopp et al., A new approach for creating defined geometries by navigated laser ablation based on volumetric 3-D data. IEEE Trans Biomed Eng. Jul. 2008;55(7):1872-80.

Tucker et al., Creation of an Automated Fluorescence Guided Tumor Ablation System. IEEE J Transl Eng Health Med. Jul. 21, 2021;9:4300109. 1-9.

Walsh et al., Pulsed CO2 laser tissue ablation: effect of tissue type and pulse duration on thermal damage. Lasers Surg Med. 1988;8(2):108-18.

Yang et al., Techniques for robot-aided intraocular surgery using monocular vision. Int J Rob Res. Jul. 2018;37(8):931-952.

Zucker et al., CHOMP: Covariant Hamiltonian optimization for motion planning. The international Journal of Robotics Research. 2013; 32(9-10):1164-1193.

* cited by examiner (b). Obstacle vector field (a). EDT distance field (a). 2D orientation planning by vector fields (b). Reverse gradient directions

SYSTEMS AND METHODS FOR 3D DATA DRIVEN LASER ORIENTATION PLANNING

RELATED APPLICATIONS

This application claims priority to and the benefit of U.S. Provisional Patent Application No. 63/291,507 filed Dec. 20, 2021, which is incorporated herein by reference in its entirety for all purposes.

GOVERNMENT FUNDING

This invention was made with government support under EB030982 awarded by the National Institutes of Health. The government has certain rights in the invention.

BACKGROUND

Robotic laser scalpels are used in different surgical tasks, such as eye surgery, neurosurgery, and dermatology. Precise control of laser energy delivery to tissues ensures optimal treatment of targeted lesions and tissue regions, making robotic control of these systems an essential element for precision laser guided surgery. A single laser pulse can create a 3D volumetric cavity on the tissue surface, and its shape is related to the laser incident angle and laser energy delivery. Incorrect orientation planning and laser energy delivery can result in damage to collateral "non-target" (e.g., healthy) tissue removal. In other words, different laser orientations can create various tissue ablation cavities, and incorrect incident angles can cause over-irradiation of healthy tissue that should not be ablated.

Robotic laser orientation problems have been widely studied in robotic laser cutting, industrial robotic manipulation, and robotic laser surgery. However, prior efforts do not minimize errant tissue overcutting based on laser incident angle. These methods generally leverage the vision or user inputs to develop an orientation planning strategy. The laser scalpel is typically affixed to the 6-DOF (degree-of-freedom) robotic arm end-effector, with the robot controlling the laser in order to move towards a predefined planning trajectory. Such robotic orientation planning can improve the safety and robustness of these surgical systems. For example, as shown in FIG. 1, different 6-DOF laser orientations can create distinct cavities and causes various effects for laser surgery.

The development of a laser orientation planner is an important problem in robotic laser surgery. However, two problems associated with the laser orientation planning include:

1) how to model the laser-tissue interaction with the laser orientation and ablation center and
2) how to use the learned laser-tissue model to design a laser orientation planner to minimize the over-irradiation of healthy tissue.

SUMMARY

The Summary is provided to introduce a selection of concepts that are further described below in the Detailed Description. This Summary is not intended to identify key or essential features of the claimed subject matter, nor is it intended to be used as an aid in limiting the scope of the claimed subject matter.

As disclosed herein, robotically controlled laser orientation is optimized to minimize errant overcutting of healthy tissue during the course of pathological tissue resection. An optimization problem is formulated to find the optimal laser orientation in order to minimize the possibility of excessive laser-induced tissue ablation. First, a 3D data-driven geometric model is developed to predict the shape of the tissue cavity after a single laser ablation. Modelling the "target" and "non-target" tissue region by an obstacle boundary, the determination of an optimal orientation is converted to a collision-minimization problem. The goal of this optimization formulation is maintaining the ablated contour distance from the obstacle boundary, which is solved by the projected gradient descent method. Simulation experiments validate the proposed method with conditions of various obstacle shapes and different initial incident angles.

As disclosed herein, an optimal laser incident orientation is described to minimize the distance between the ablated profile and a pre-defined obstacle boundary. This boundary can be defined as either a preoperative "edge" between healthy and non-healthy tissue, or a pre-designed cavity contour with a fixed geometry.

As disclosed herein, an optimization model is provided to solve the robotic laser orientation planning problem with an application of minimizing the over-cutting of healthy tissue for robotic laser surgery. The laser-tissue cavity can be predicted under various incident angles and the orientation planning can be guided by the reference vector field. With this method, the surgeon can manually define a preoperative boundary or a 3D contour, and the planner can calculate an optimal incident angle to minimize the probability of cutting incorrect tissue regions during surgery.

One aspect of the present disclosure provides a method of controlling a robotic laser orientation angle for surgical planning and simulation, with application for biological laser-tissue resection. The method develops a laser-tissue geometric model by using a 3D data driven method (e.g., Gaussian function fitting for parameter estimation). A laser-tissue kinematic model estimates the depth of cut based on the ablation center on the biological tissue surface. The analytical gradient of the laser-tissue kinematic system is derived and used to formulate an optimization problem, which is solved with a gradient-based method.

In one aspect, the present disclosure provides a method comprising ablating a substrate with a laser at an orientation to create a cavity in the substrate, scanning the cavity, and creating a three-dimensional surface for the cavity. The method further includes storing the three-dimensional surface in a dataset. The dataset includes a laser projected distance as an independent variable and a depth of cut as a dependent variable. The method further includes fitting parameters of a gaussian-based model for the laser and the substrate based on the dataset.

In some embodiments, the orientation is a first orientation, the cavity is a first cavity, the three-dimension surface is a first three-dimensional surface, and wherein the method further includes: ablating the substrate with the laser at a second orientation to create a second cavity in the substrate; scanning the second cavity; creating a second three-dimensional surface of the second cavity; and storing the second three-dimensional surface in the dataset.

In some embodiments, the substrate is a biological tissue.

In some embodiments, scanning the cavity is with optical coherence tomography or micro computed tomography.

In some embodiments, the method further includes creating a sequence of cross-sectional images of the cavity.

In some embodiments, the sequence of cross-sectional images is filtered, segmented, and concatenated to create the three-dimensional surface for the cavity.

In some embodiments, the method further includes predicting a post-ablation surface using the gaussian-based model.

In some embodiments, predicting the post-ablation surface includes providing a pre-ablation profile and a set laser orientation.

In some embodiments, the method further includes projecting a point on the pre-ablation surface to a laser reference plane and calculating a projected distance to a laser center on the gaussian-based model.

In some embodiments, the method further includes determining a predicted depth of cut based on the projected distance to the laser center.

In some embodiments, the method further includes collecting predicted depth of cuts for all points on the pre-ablation surface to generate the predicted post-ablation surface.

In one aspect, the present disclosure provides a method comprising providing a pre-ablation surface; labeling a three-dimensional obstacle boundary that separates material to be remove by a laser and material to remain; and determining an orientation of the laser that results in a predicted post-ablation surface that does not intersect the three-dimension obstacle boundary.

In some embodiments, the method further includes predicting a plurality of post-ablation surfaces for a plurality of orientations of the laser.

In some embodiments, predicting the plurality of post-ablation surface utilizes a gaussian-based model for the laser.

In some embodiments, the method further includes generating a Euclidean distance transform metric for each of the plurality of post-ablation surfaces.

In some embodiments, the Euclidean distance transform metric is a measurement of a distance between a query point on the post-ablation surface to the closest point on the three-dimensional obstacle boundary.

In some embodiments, a raw distance value from the Euclidean distance transform metric is post-processed to an oriented distance value with a negative value if the query point crosses the three-dimensional obstacle boundary.

In some embodiments, the Euclidean distance transform metric is converted to an obstacle cost.

In some embodiments, the obstacle cost is minimized with a gradient-based constrained optimization method.

In some embodiments, determining the orientation of the laser that results in the predicted post-ablation surface that does not intersect the three-dimension obstacle boundary includes maximizing a Euclidean distance transform metric between the predicted post-ablation surface and the three-dimensional obstacle boundary.

In some embodiments, the method further includes moving the laser to the orientation and energizing the laser.

In some embodiments, the pre-ablation surface is tissue, the three-dimensional obstacle boundary separates tissue to be remove by the laser and tissue to remain; and wherein the laser is energized for laser-tissue resection.

BRIEF DESCRIPTION OF THE DRAWINGS

The accompanying figures are provided by way of illustration and not by way of limitation.

FIG. 5A is a schematic of the laser-tissue geometric model. FIG. 5B is a graph of a learned geometric gaussian profile.

FIG. 6A illustrates Micro-CT cavities point cloud. FIG. 6B illustrates three-dimensional cavities under various laser incident angles. FIG. 6C illustrates training data to fit the gaussian profile FIG. 6D illustrates the learned geometric gaussian profile.

FIG. 9A illustrates examples of controlling the angles to follow a reference trajectory in the horizontal (XY plane) directions.

FIG. 9B illustrates examples of controlling the angles to follow a reference trajectory in the vertical (Z-axis) direction.

FIG. 10A shows an example case of controlling the incident angle within a range by the projected gradient descent method (Proj-GD). FIG. 10B shows the point robot trajectories for Test 2. FIGS. 10C, 10D, 10E, and 10F show the volumetric tissue removal before and after orientation planning, with a Gaussian-shape obstacle boundary.

DETAILED DESCRIPTION

Figure 1:
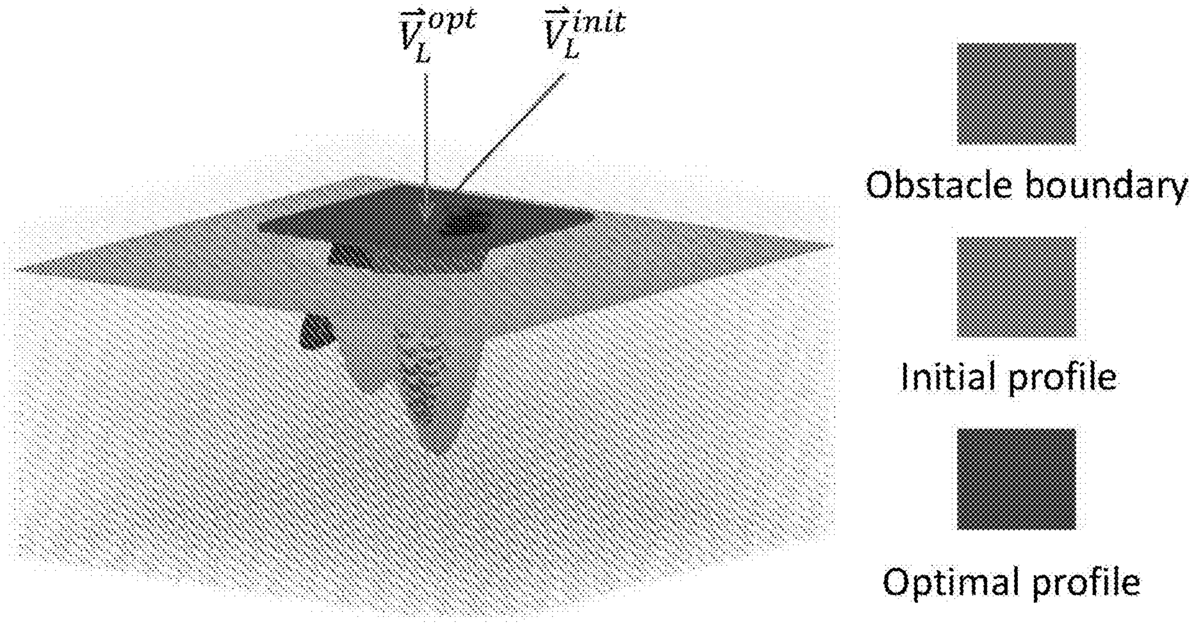
FIG. 1 illustrates a three-dimensional obstacle boundary and two three-dimensional ablated contours created by two laser orientations.

Section headings as used in this section and the entire disclosure herein are merely for organizational purposes and are not intended to be limiting.

All publications, patent applications, patents and other references mentioned herein are incorporated by reference in their entirety.

1. DEFINITIONS

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "subject" and "patient" as used interchangeably herein and refer to both human and nonhuman animals. In some embodiments, the subject comprises a human who is undergoing a procedure using a system or method as prescribed herein. The subject or patient may be undergoing various forms of treatment.

As used herein, the term "pre-ablation surface" refers to the original surface of the exposed tissue, and this is a 3D contour. For example, in neurosurgery, the pre-ablation surface is the exposed portion of the tumor tissue. As another example, in eye surgery, the pre-ablation surface is the exposed surface of the cornea.

As used herein, the term "post-ablation surface" refers to an 3D surface that is updated after a one-shot laser-tissue ablation to the pre-ablation surface.

As used herein, the term "3D query point" refers to one of the 3D points at the pre-ablation tissue surface.

As used herein, the term "depth of cut" refers to the distance between the pre-ablation surface and the post-ablation surface of a 3D query point towards the laser incident orientation.

As used herein, the term "laser reference plane" refers to a synthetic plane defined by a laser incident orientation and a reference center. The reference center is determined by projecting a surface point (e.g., the one that shows the greatest depth of cut) towards the laser incident orientation. The laser incident orientation and the reference center can thus formulate a synthetic reference plane as a representation of the laser energy profile. The symmetric Gaussian-based profile represents that the closer to the laser origin (e.g., the center of the Gaussian function), the greater the energy received and longer depth of cut.

As used herein, the term "laser projected distance" refers to the distance between the projected coordinate and the reference center (both at the laser reference plane). Given a specific laser incident orientation, a 3D query point can be projected to a laser reference plane, thereby determining a 2D projected coordinate. The distance between the projected coordinate and the reference center is calculated as the laser projected distance.

As used herein, the term "Gaussian-based model" refers to a standard 3D bell-shaped Gaussian function parameterized by a standard deviation and an amplitude.

As used herein, the term "safe tissue region" refers to the volume of tissue that can be removed. For example, the tumorous region in brain surgery or the volume of tissue to be removed during a corneal reshaping in ophthalmic surgery.

As used herein, the term "un-safe tissue region" refers to surrounding or underlying healthy tissue that should not be removed during a procedure and is protected by employing the methods detailed herein.

As used herein, the term "obstacle boundary" refers to the intersection of the safe tissue region and the un-safe tissue region. In some embodiments, the obstacle boundary is the boundary of the tumor where it touches healthy tissue. In other embodiments, the obstacle boundary is a synthetic boundary between the area to be removed and the area to be left in place after a corneal reshaping surgery.

As used herein, the term "voxel" refers to the smallest unit of volume in a volumetric 3D image, such as those collected from biomedical imaging systems (e.g., MRI, optical coherence tomography, CT, etc.). A voxel is akin to a pixel in a 2D image, but for a 3D image.

Unless otherwise defined herein, scientific and technical terms used in connection with the present disclosure shall have the meanings that are commonly understood by those of ordinary skill in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. LASER-TISSUE GEOMETRIC MODEL

The laser-tissue geometric model refers to a system capable of predicting the ablated tissue contour under a given laser incident angle. Given a 3D point on the tissue surface, the model disclosed herein predicts the depth-of-cut, and thus estimates the new position after tissue removal. The main modelling approaches can be categorized as Model-based and Model-free methods.

Model-based methods estimate the ablated contour by calculating the energy delivery for each tissue position. Material removal is then predicted based on the energy incident at each point on the surface and an ablation rate. However, modelling the complex physics for laser-tissue interaction (e.g., thermal effect, optical property, etc.) is difficult and prone to different experimental conditions such as water spray, surface geometry and tissue material.

Model-free methods model the tissue removal by using an entirely data-driven approach. Data driven approaches are advantageously because it is difficult to model the laser-tissue interaction due to the heterogeneity of tissue material and the complex physical mechanism. The laser beam profile can be modelled by a Gaussian function. The tissue of removal should follow the similar pattern since the depth-of-cut is related to the strength of energy delivered to the target. Therefore, the Gaussian-based model is used to describe the laser-tissue relation, and the parameters of the Gaussian function can be learned through the 3D cavity data collected. In some embodiments, the 3D cavity data is collected by high resolution scanners such as confocal microscopy and computed tomography (CT).

The method of learning laser-tissue physics by Gaussian function fitting is applied in various robotic laser applications, such as tissue depth control, surgical simulation, and generating a cutting path for volumetric resection. However, these studies have not discussed the problem of laser orientation planning with various laser angles and controlling the ablated profiles for robotic laser surgery, which is detailed herein.

Figure 5A:
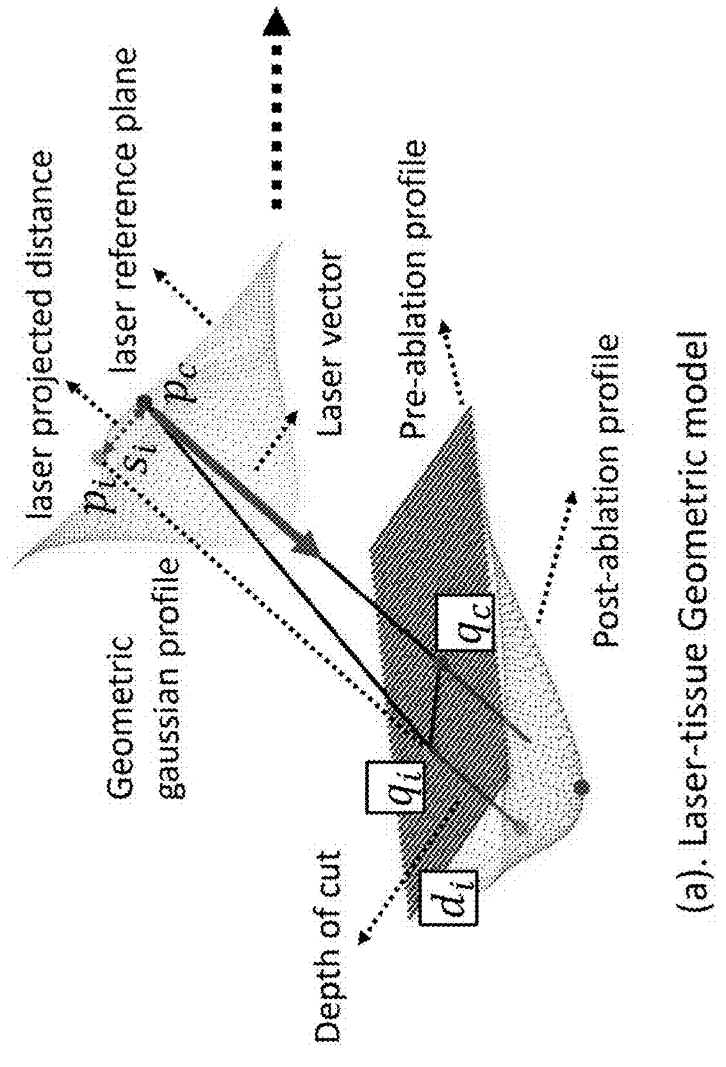
FIGS. 5A and 5B illustrate the laser-tissue kinematic modelling.
Figure 5B:
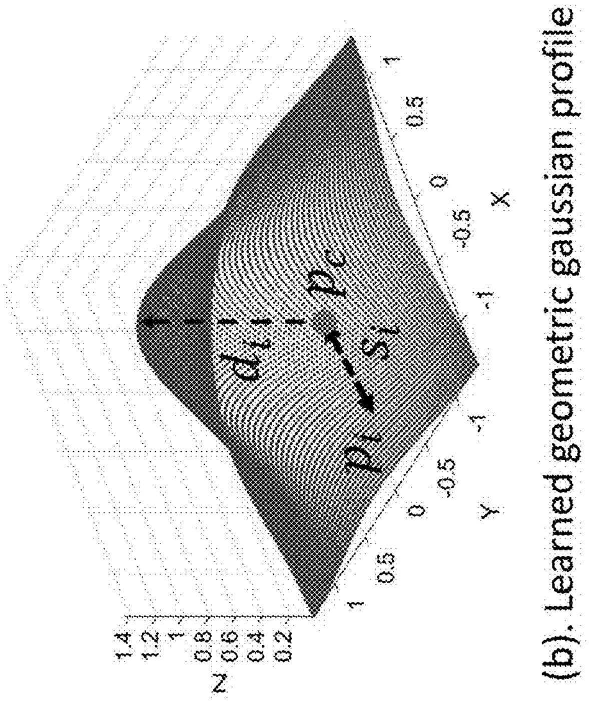
Figures 6A, 6B, 6C, 6D:
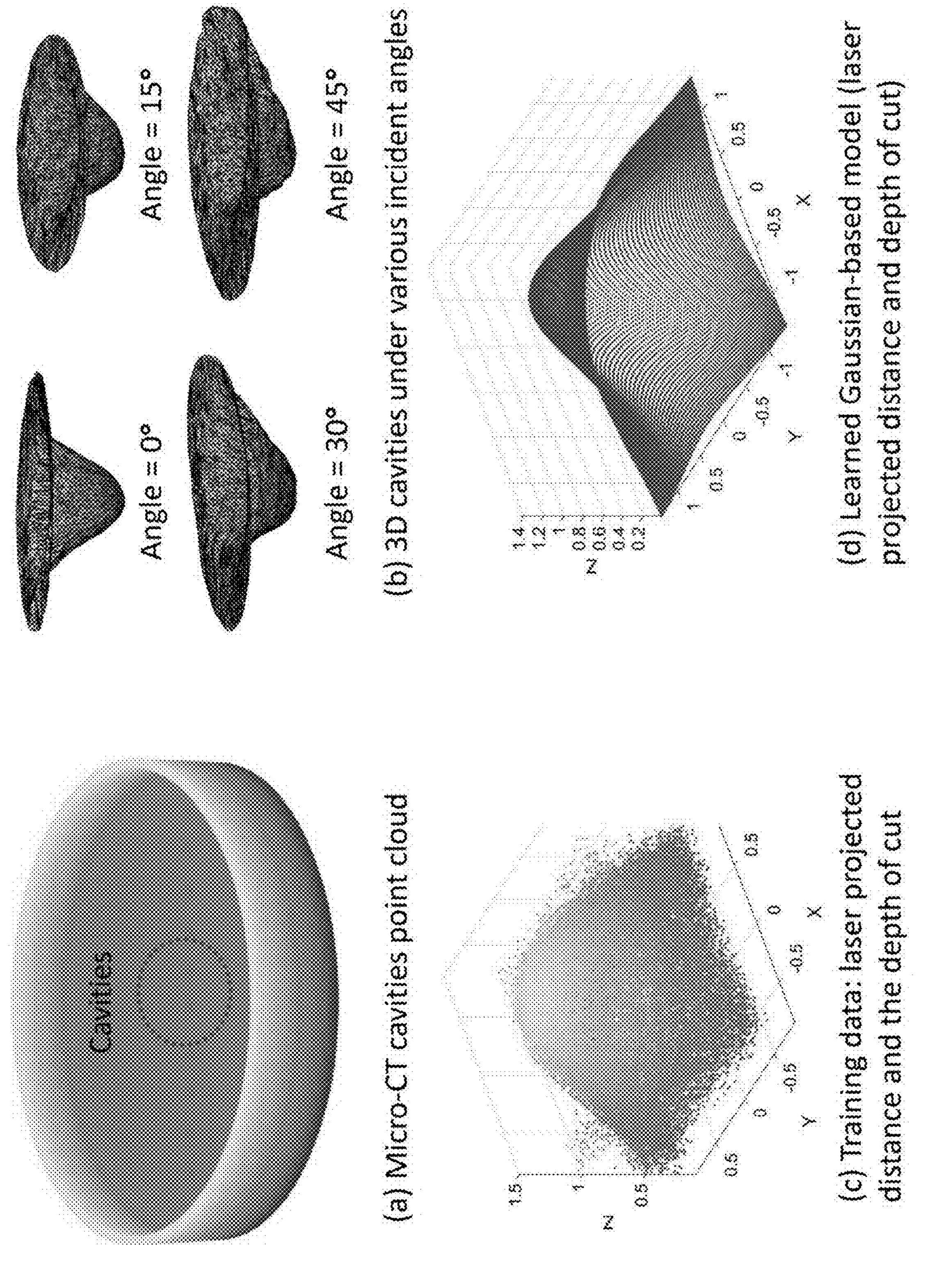
FIG. 6A-D illustrate parameter estimation by Micro-CT data.

Gaussian Profile. In some embodiments, the laser is a $CO_2$ laser with a wavelength of approximately 10.6 μm and a $1/e^2$ spot size of approximately 0.80 mm. The $CO_2$ beam profile can be generally described by a Gaussian function. FIG. 5A illustrates the complete 3D geometric model. The depth-of-cut for a surface position depends on the strength of the laser energy and thus follows the Gaussian pattern. FIGS. 5A and 5B illustrate the geometric configuration of the laser-surface model and the Gaussian-shape $CO_2$ beam profile. While a $CO_2$ laser is utilized for demonstrative purposes, this approach can be generalized to other laser scalpels that likewise have Gaussian beam profiles.

To model the laser-tissue geometry, a "laser reference plane" is defined with the laser center and the orientation vector, where the laser center aligns with the surface point that shows the greatest depth of cut. The surface points can be projected to this plane to estimate the depth-of-cut. A region of interest (ROI) is defined on the superficial tissue surface. In this configuration, $q_c \in \mathbb{R}^3$ denotes the laser ablation center on the 3D surface and $q_i \in \mathbb{R}^3$ is a query point around this ablation center, with EQN. 1.

$$p_c = q_c - v * L_{ref} \quad [1]$$

Where $q_c \in \mathbb{R}^3$ is defined as the laser incident center and $v \in R^3$ is the incident vector. The operator $\|\cdot\|_2$ refers to the L2-norm and typically restricted to $\|v\|_2=1$. $L_{ref}$ is a reference distance that can be set as an arbitrary constant, since the geometric configuration does not depend on this value (set as "1").

The depth-of-cut $d_i$ for the surface point $q_i$ is defined as the tissue removal at the incident direction. Based on the Gaussian beam profile assumption, $d_i$ can be calculated by the projected distance $s_i$ between $p_i$ and $p_c$ as EQN. 2.

$$d_i = L_G * \exp\left(\frac{s_i^2(v, q_i)}{-2 * \sigma_G^2}\right) \quad [2]$$

Where exp(·) is an exponential operator. The geometric gaussian profile is assumed symmetric and the parameters of $L_G$ and $\sigma_G$ can be estimated by the data-driven method for a specified tissue material and laser setting.

Another important task is to determine $s_i$, which is the altitude of the triangle with the sides of $p_c$ and $q_c$, as EQN. 3.

$$\frac{s_i * c}{2} = \sqrt{h(h-a)(h-b)(h-c)} \quad [3]$$

Where $\sqrt{h(h-a)(h-b)(h-c)}$ is the triangle area denoted by the three sides $$a(\cdot) = \|q_c - q_i\|_2;\ b(\cdot) = \|q_i - q_c + v(\theta) * L\|_2;$$

$c(\cdot)=\|p_c-q_c\|_2=L=1$, and have $$h = \frac{a+b+c}{2}.$$

Data-driven Method for Gaussian Function Parameters. Given a laser-tissue geometric model, the amplitude $L_G$ and variance parameter $\sigma_G$ are estimated. In practice, the amplitude is a function of laser power, time, and the optical properties of the tissue that drive ablation. Herein, any ablation amplitude is assumed achievable by tuning the laser parameters and thus considered as a controllable variable. The $L_G$ and $\sigma_G$ can be function-fitted with the 3D data collected by high-resolution scanner. Micro-CT data is used to characterize the laser-tissue cavities under various incident angles for 2D and 3D analysis.

A dataset of 3D measurements from a list of 3-DOF orientation angles $\{\theta_i\} \in \mathbb{R}^3$. Each laser pulse at $\theta_i$ can create a tissue cavity described by the Micro-CT point cloud data, which is defined as $\{q_{i,j}\} \in \mathbb{R}^3$. The i refers to the index of incident angle and j as the index of measurement. The point cloud can be converted to the projected coordinates at the laser reference plane and this is referred as $\{s_{i,j}\} \in \mathbb{R}^3$.

With each $s_{i,j}$, the depth-of-cut $d_{i,j}$ can be calculated by EQN. 2 and obtain $\{d_{i,j}\} \in \mathbb{R}^3$. Therefore, a dataset $\{s_{i,j}, d_{i,j}\} \in \mathbb{R}^3$ is obtained, which can be used to estimate the Gaussian function parameters ($L_G$ and $\sigma_G$). In some embodiments, the function fitting is achieved by using the log operation and the nonlinear least-squares fitting metric. FIG. 6A-D illustrates the Gaussian parameters fitting procedure.

At the end of model tuning, a function is provided that is parametrized by laser parameters and laser incident angle, which can accurately predict the geometric shape of a crater created by a one-shot laser ablation in the target tissue. This model is specifically tuned for the tissue the interrogation cut was made it. Thus, if this method is being used in a surgery, the function is specific to that patient's tissue (e.g. tumor).

In one embodiment, the method includes (STEP 1) perform an interrogation cut with a single laser ablation in the tissue at a known angle of incidence. (STEP 2) acquires a profile (e.g., a 3D image") of the created cavity with a 3D imaging system. In some embodiments, the 3D image is created by concatenating multiple 2D images scanned from the 3D imaging system, such as a biomedical imaging system (MRI, CT, Optical Coherence Tomography). (STEP 3) in some embodiments includes performing image processing steps on the 3D image to prepare it for algorithm use. In some embodiments, the image processing includes smoothing the image, noise filtering, and other suitable image processing operations. (STEP 4) includes extracting geometric parameters from the acquired 3D image of depth of cut and the laser projected distance to prepare for data-driven model fitting. These two parameters formulate a geometric relation about how a laser orientation angle can affect the shape of the surface cavity created. The crater shape (e.g., depth of cut) from the 3D image acquired and the laser projected distance (e.g., distance between the surface-to-plane projected point to the center of the laser origin). The "depth of cut" is the distance between the pre-ablation and post-ablation surface points. The "projected distance" is measured by first projecting a surface to a reference plane defined by the laser origin and the incident orientation to get a projected coordinate, and secondly, calculating the distance between the projected coordinate and the laser origin (at the reference surface). (STEP 5) includes fitting a Gaussian-based model to the geometric parameters of the cavity. The Gaussian beam is assumed to be symmetric and normally distributed function described by two scalar parameters: amplitude and variance. The regression problem (e.g., Gaussian function fitting to find the amplitude and variance) performs over all the points within the cavity. Each point is considered as a unique data point to fit the model.

The result of the method disclosed herein is a tuned function that is parameterized by laser parameters (e.g. wavelength, pulse time or irradiance time, spot size, and power profile which is assumed to be Gaussian in this case) and incident angle for the specific tissue being cut. This method does not require the complex physical modelling associated with the heat transfer, chemical reaction and optical tissue property, and but rather solves the non-linear regression problem. As mentioned, modelling the laser-tissue interaction is a difficult problem due to the heterogeneity of tissue material and the complex physical mechanism. The data-driven method disclosed herein encodes the physical mechanism into the geometric model and can be uniquely adjusted to different tissue material. The learned laser-tissue interaction model plays an important role in the design of laser orientation planner with numerical optimization approaches. Optimizing the laser orientation can show potential applications of minimizing errant overcutting of healthy tissue during the course of pathological tissue resection.

In some embodiments, the method disclosed herein is used with other surgical laser systems with lasers of different wavelengths and power profiles shapes other than gaussian, such as those equipped with Nd:YAG and Er:YAG lasers or lasers with flat-top beam profiles.

Laser-Tissue Kinematic System. The laser-tissue geometric model can be referred as a kinematic system that describes the relation between the laser incident angle and the resulting ablation contour. For a given incident direction, this contour is formulated by the surface sampled points after the tissue removal. For each surface point $$q_i^k \in \mathbb{R}^3$$

at k-th time step, results in EQN. 4.

$$q_i^{k+1}(v, q_i^k) = q_i^k + v * d_i \tag{4}$$

Where $$d_i = L_G * \exp\left(\frac{s_i^2(v, q_i^k)}{-2 * \sigma_G^2}\right)$$

from EQN. 2.

$$q_i^{k+1} \in \mathbb{R}^3$$

is the updated position from $$q_i^k.$$

The $L_G$ and $\sigma_G$ are the learned Gaussian function parameters. The $$s_i(v, q_i^k)$$

depends only on v and $q_i$. This kinematic system can be used to predict new surface profiles given the initial surface point cloud and the incident angle.

The data-driven Laser-tissue interaction model is used to formulate the kinematics to update the shape of the laser-tissue cavities. Each query point, as considered as a small robot system, can formulate a kinematic model where the given laser orientation and ablation center can be mapped to a new positioning output. The summation of new positions of all the 3D query points at the surface equal to a new surface cavity to show the resulting effect of the laser-tissue interaction. Method steps include: (STEP 1) For each 3D query point at the pre-ablation surface, project the point to the laser reference plane. This can be used to calculate the projected distance to the center of the laser origin. (STEP 2) The laser projected distance is served as an input to the data-driven laser-tissue model and mapped to an output of the depth of cut. (STEP 3) A kinematic model is used the predicted depth of cut to describe the positioning output. (STEP 4) the new positions of all the query points at the surface and formulate the post-ablation laser cavity.

3. LASER ORIENTATION OPTIMIZATION

Figure 2:
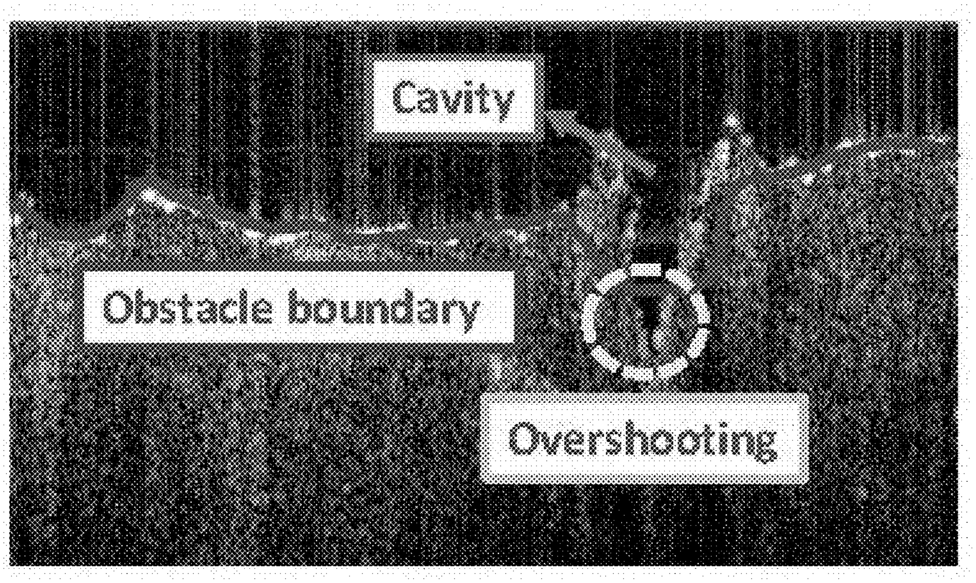
FIG. 2 is a two-dimensional image of laser-tissue model illustrating an ablated contour outside the labelled boundary (e.g., with overshooting).

In some embodiments, the optimal laser orientation problem is modelled as an "Obstacle avoidance" planning problem by which the ablated contour, as created by the current laser angle, should keep the adequate distance to the pre-defined boundary (between "target" and "non-target" tissue region). For example, in FIG. 2, an ablated contour of a single laser pulse is located outside of a pre-designed boundary, which can be measured in OCT slice image. These images can be concatenated to formulate a 3D point cloud and thus the 2D obstacle boundary can become a 3D surface.

Figure 3A:
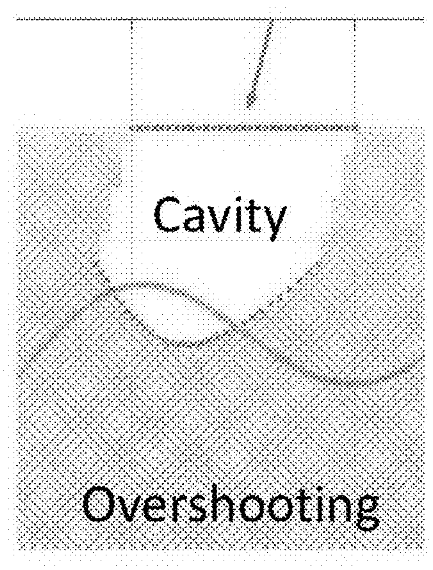
FIG. 3A is a two-dimensional schematic for a tissue removal cavity that crosses the obstacle boundary (e.g., overshooting).
Figure 3B:
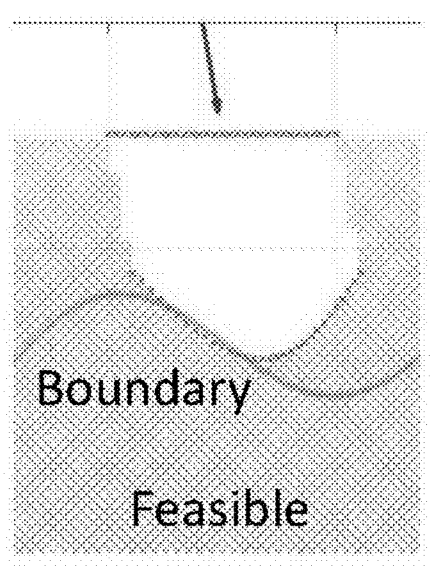
FIG. 3B is a two-dimensional schematic for a tissue removal cavity that does not cross the obstacle boundary.
Figure 4:
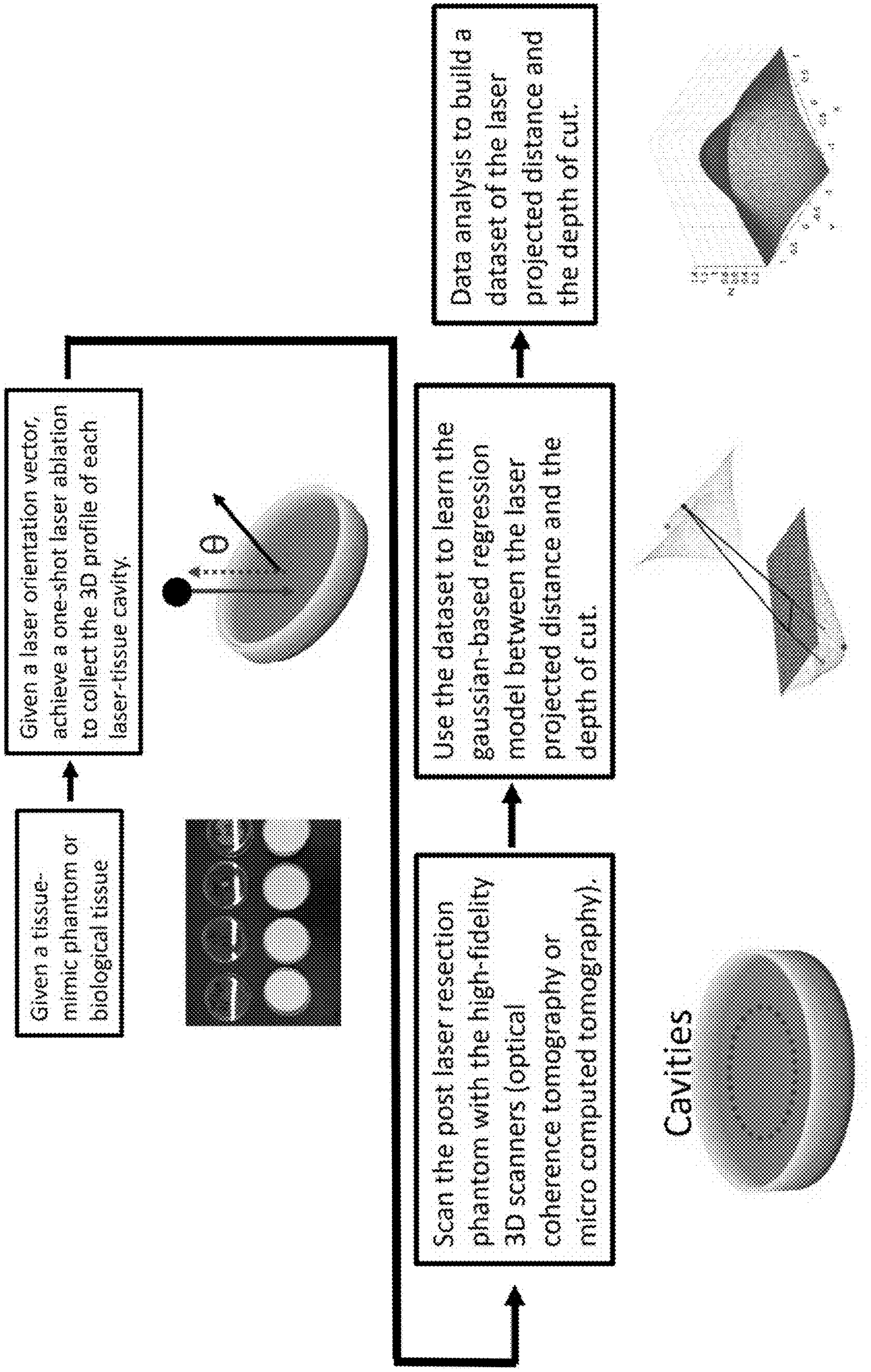
FIG. 4 is a workflow of a method for generating a three-dimensional data-driven laser-tissue model.

Given a pre-defined obstacle boundary and a laser-tissue geometric model, the goal is to find an optimal laser orientation that creates a collision-free ablation contour. FIGS. 3A and 3B depicts over-cutting and feasible ablation in 2D. In some embodiments, the obstacles are modelled by the Euclidean distance transforms (EDT) and the signed distance, which can be used to formulate a 3D voxel field that encodes the collision information (e.g., distance to the obstacle boundary). These distance fields can be employed to guide the orientation planning.

Collision Modelling with Obstacle Boundary. Regarding the EDT field, in some embodiments, the goal is to find an optimal laser orientation that can maintain the distance between the ablated contour and the obstacle boundary. The obstacle boundary is modeled by the Euclidean distance transforms (EDT). EDT represents the distance to the nearest obstacle position for each 3D voxel, which can be used to measures the level of collision for an arbitrary 3D position.

Figure 7B:
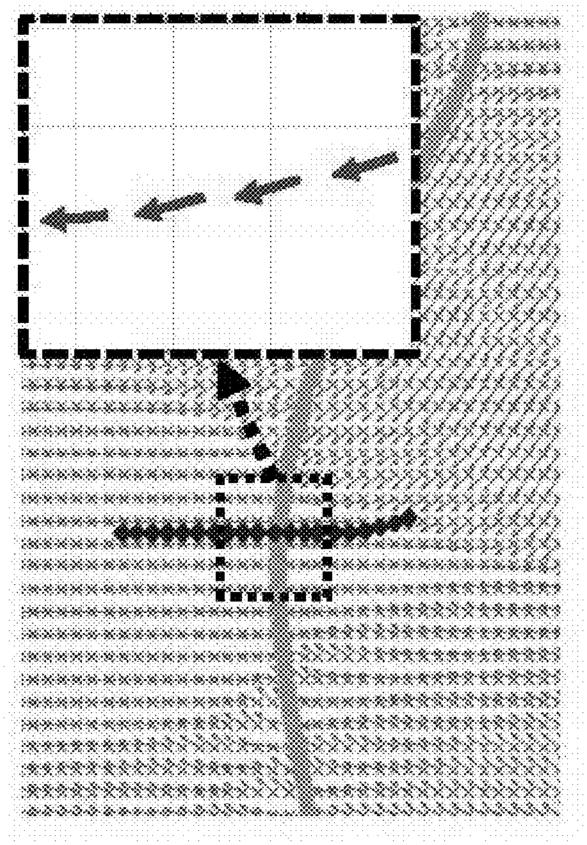
FIG. 7B illustrates a two-dimensional obstacle vector field.
Figure 7A:
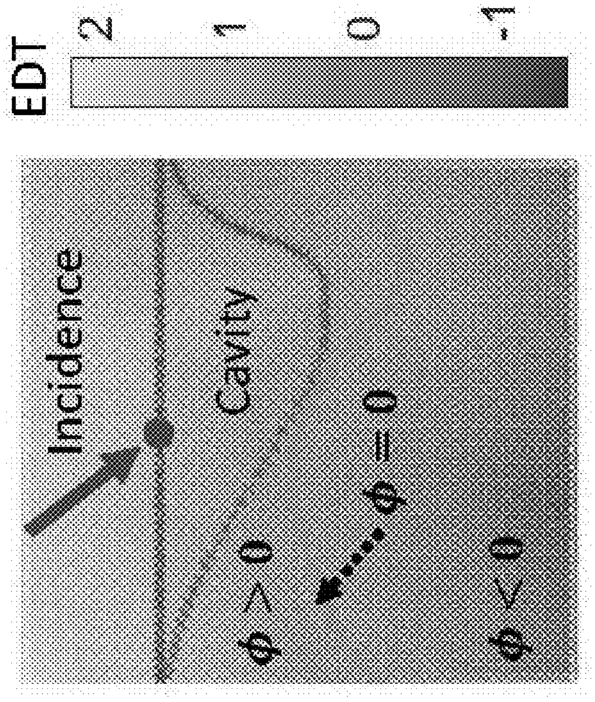
FIG. 7A illustrates a two-dimensional EDT value distance field.

Regarding obstacle modelling, the obstacle boundary can be considered as a 3D surface where the EDT value is zero. Specifically, $\Phi(\cdot)$ is defined as the EDT levelset function and $\Phi(\cdot)=0$ denotes the boundary positions. $\Phi(\cdot)>0$ denotes the target region and $\Phi(\cdot)<0$ denotes the non-target region, as shown in FIG. 7A. An EDT vector field $\nabla\Phi(\cdot)$ can be calculated by the directional gradients with the, for example, 3D Sobel gradient operator. $\nabla\Phi(\cdot)$ denotes a direction of the lower collision cost and thus can be used to guide the orientation planning. In some embodiments, the obstacle cost $C(\Phi(x))$ is defined as a piecewise function of EQN. 5.

$$C(\Phi(x)) = \begin{cases} -\Phi(x) + \frac{1}{2}\epsilon & \Phi(x) \le 0 \\ \frac{1}{2\epsilon}(\Phi(x) - \epsilon)^2 & 0 < \Phi(x) \le \epsilon \\ 0 & \Phi(x) > \epsilon \end{cases} \quad [5]$$

Where $\epsilon$ is the obstacle distance threshold; $\Phi$ is the EDT value and x is the 3D voxel position. The gradient of the cost function $$\nabla C(\Phi) = \frac{\theta C}{\theta \Phi}$$

is negative if the position is getting closer to the obstacle boundary, which will guide the point to move to a reverse direction. FIG. 7A illustrates the EDT values distribution in 2D. The EDT can be set as positive and negative inside and outside the obstacle boundaries. FIG. 7B depicts the vector trajectory around the boundary, which can guide the point movement towards the positive EDT region.

Orientation Planning Algorithm. The orientation planning minimizes the total obstacle costs for the ablated contour. The contour can be represented by a point cloud data that can be collected by any intraoperative 3D sensors. In practice, a laser incident orientation is usually perpendicular to the point of interest and is only allowed to adjust to a small angle. A constrained optimization problem is formulated as EQN. 6.

$$\min_{\theta \in \mathbb{R}^3} f = \sum_i C(\Phi(q(v(\theta), q_i))) \quad [6]$$

$$\text{s.t. } \theta_1 \le \theta \le \theta_2$$

This objective function $f(\cdot)$ denotes the summation of obstacle costs for each point at the ablated contour. The incident orientation $v(\theta)$ is controlled by the angle vector $\theta \in \mathbb{R}^3$. The $C(\cdot)$ represents the obstacle cost at the current 3D voxel position. $\Phi(\cdot)$ is the EDT distance function. $Q(\cdot)$ is the function operator following the kinematic model in EQN. 4. $\Theta_1$ and $\theta_2$ describe the 3-DOF angle range. As the ablation center $q_c$ is fixed, the laser orientation $v(\theta)$ is related to the incident angle and the surface point $q_i$.

Regarding Analytical gradient, the analytical gradient of the objective function is important for the optimization solver and can be derived by chain rule. $\nabla C(\cdot)$ and $\nabla\Psi(\cdot)$ can be obtained by EQN. 5 and the EDT field. For $\nabla q(\theta)$, the kinematic system model q( ) is simplified and rewritten as EQN. 7.

$$q = q_i + v(\theta) * L_G * \exp(\mu(v(\theta))) \quad [7]$$

Where $$\mu(v(\theta)) = \frac{s_i^2(v(\theta, q_i))}{-2 * \sigma_G^2}.$$

To take the derivative of q(_) with respect to the incident angle $\theta$, EQN. 8.

$$J = \frac{\partial q}{\partial \theta} = \frac{\partial q}{\partial v} * \frac{\partial v}{\partial \theta} = \begin{bmatrix} \frac{\partial q_1}{\partial \theta_1} & \frac{\partial q_1}{\partial \theta_2} & \frac{\partial q_1}{\partial \theta_3} \\ \frac{\partial q_2}{\partial \theta_1} & \frac{\partial q_2}{\partial \theta_2} & \frac{\partial q_2}{\partial \theta_3} \\ \frac{\partial q_3}{\partial \theta_1} & \frac{\partial q_3}{\partial \theta_2} & \frac{\partial q_3}{\partial \theta_3} \end{bmatrix} \quad [8]$$

The J is the Jacobian matrix of the system model and each item is $$\frac{\partial q_i}{\partial v_j} = \sum_{t=1,2,3} \frac{\partial q_i}{\partial v_t} * \frac{\partial v_t}{\partial \theta_j}$$

(I and j are index of the item in J). Also, EQN. 9.

$$\frac{\partial q}{\partial v_j} = \frac{\partial q_i}{\partial v_j} + \frac{v_i}{v_j} * L_G * \exp(\mu(\cdot)) + \frac{\partial}{\partial v_j}(\exp(\mu(\cdot)) * L_G * v_i) \quad [9]$$

$$\frac{\partial v_j}{\partial \theta_j} = \frac{\partial}{\partial \theta_j}(R_x(\theta_x) * R_y(\theta_y) * R_z(\theta_z)) * v_0$$

Where $R_x$, $R_y$ and $R_z$ are the rotation angles that control the initial orientation vector $v_0$. The $$\frac{\partial v_j}{\partial \theta_j}$$

can be obtained by taking the derivative for the rotation matrix. The $$\exp(\mu(\cdot)) = \exp\left(\frac{s_i^2(v(\theta, q_i))}{-2 * \sigma_G^2}\right)$$

is a scalar function of $s_i(\ )$. Finally, the analytical gradient $\nabla f(\theta, q_i)$ is obtained for the objective function as EQN. 10.

$$\nabla f(\theta, q_i) = \sum_i \frac{\partial C}{\partial \Phi} * \frac{\partial \Phi}{\partial q} * \frac{\partial q(\theta, q_i)}{\partial \theta} \quad [10]$$

Where $$\frac{\partial q(\theta, q_i)}{\partial \theta}$$

is the Jacobian matrix in EQN. 9 and can be calculated from EQN. 9.

Figure 8A:
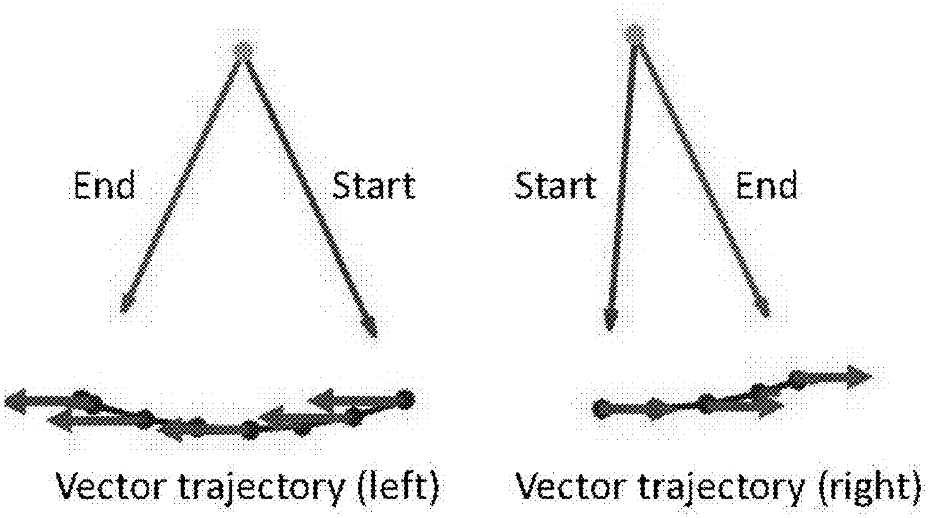
FIG. 8A illustrates two-dimensional orientation planning by vector fields.
Figure 8B:
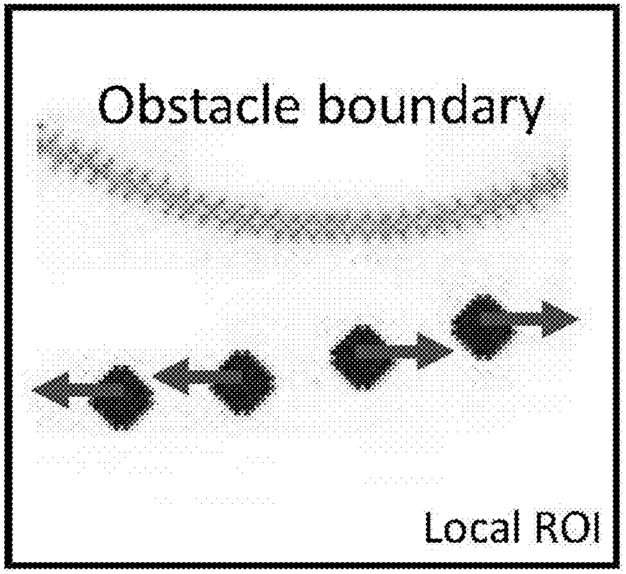
FIG. 8B illustrates reverse gradient directions.
Figures 10A, 10B, 10C, 10D, 10E, 10F:
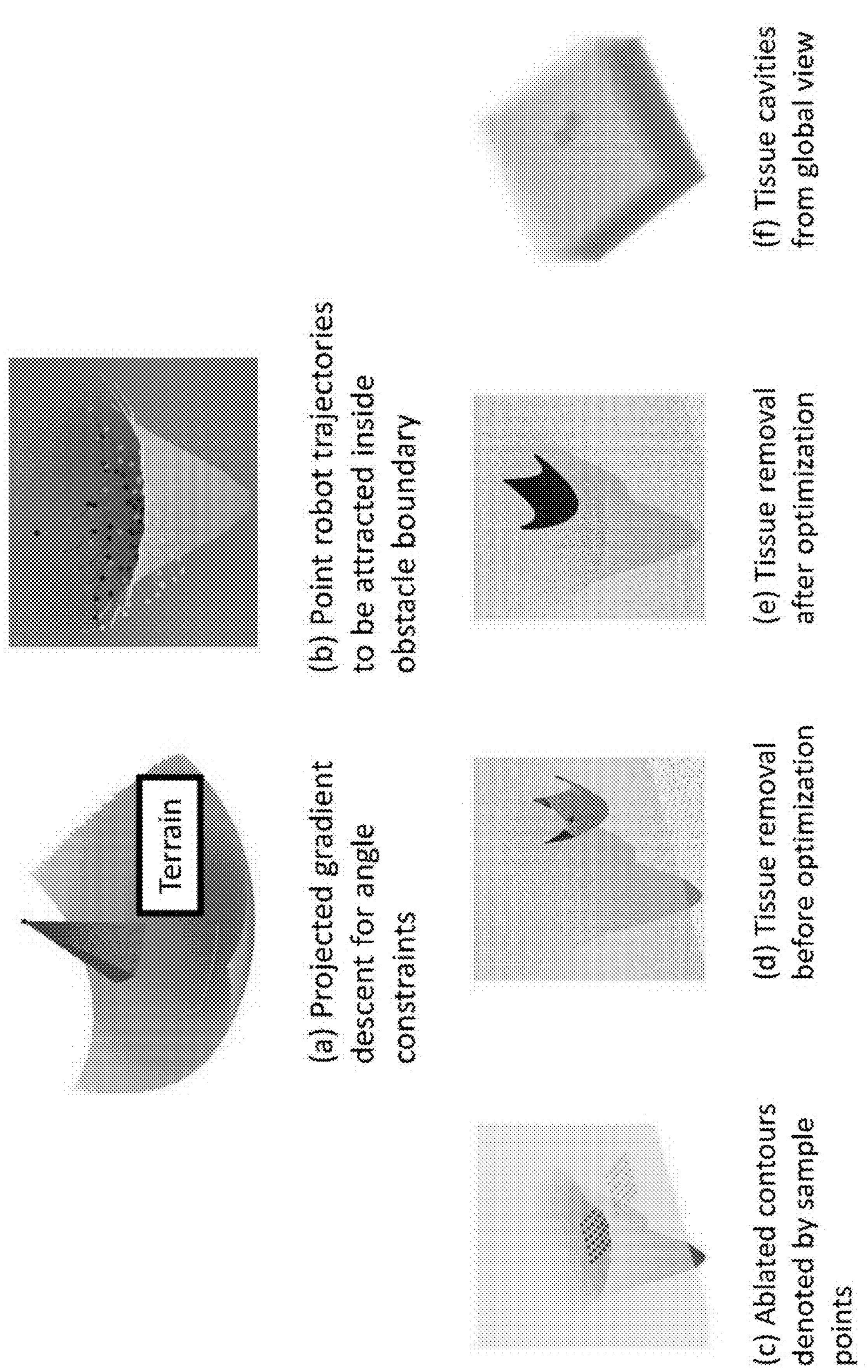
FIG. 10A-10F illustrate 3D diagrams of Test 2 (Example 2) and Test 3 (Example 3).

Regarding the projected gradient descent, for the incident angle constraint, the Projected gradient descent method, referred to as Proj-GD, is used in some embodiments to solve the optimization problem. For each iteration, Proj-GD first computes the gradient update as EQN. 11.

$$\theta^{k+1} = \theta^k - \alpha * \nabla f(\theta) \quad [11]$$

Where $\alpha$ is the step size for the gradient update. For the angle constraint, Proj-GD finds a new update by solving a quadratic optimization problem of EQN. 12.

$$\theta_*^{k+1} = Proj(\theta) = \underset{\theta_1 \le \theta \le \theta_2}{\arg\min} \frac{1}{2} \|\theta - \theta^{k+1}\|_2 \quad [12]$$

Where $\theta^{k+1}$ is from EQN. 11 and $$\theta_*^{k+1}$$

denotes the final gradient after Proj-GD. The Proj(_) is the operator for Projected gradient descent and it represents the nearest feasible point to gradient-updated position. An example of Proj-GD is depicted in FIG. 10A. Regarding data selection for each iteration. The $\nabla f(\theta)$ denotes the summation of gradients for each data point. Each gradient depends on the unique configuration of the surface position $q_i$ and the incident direction, which can be calculated differently. It is likely that some gradients are contradicted and pointing at the reverse directions and a 2D reverse gradient example is depicted in FIG. 8B. This will cause inaccurate updates and the ablated contour would be stuck in a local and sub-optimal region. Another problem is that some sample points will move to the positions with zero costs and during the optimization these points need to be selected. Therefore, a data selection approach is proposed to solve both problems. For each point robot, the reduction gain is calculated of the collision cost $c_i$ based on the updated angle $$\theta_*^{k+1}$$

as EQN. 13.

$$\text{gain}(\theta^k) = C(\theta_*^{k+1}) - C(\theta^k) \quad [13]$$

For each iteration, the gain is ranked with an increasing order and select the Top-N sample data (N can be set as 30% of the sample data). This method ensures the adequate cost reduction and guarantees that effective sample points could be selected to guide the laser orientation planning.

As detailed herein, once a model is tuned via the method described above, it can be used to optimize ablation cuts thereby optimizing surgical planning. This requires defining an "obstacle boundary", usually based on where the final desired shape of the tissue surface is (in the case of tumor surgery this is the boundary of the tumor, in eye surgery this is the final shape of the cornea). The obstacle boundary is defined by the surgeon, where the final desired shape should be located inside this boundary (otherwise it will cut healthy tissue outside of the "safe region", referred as "overcutting"). In essence, given a target geometric profile, the surgeon (or surgical system) can now use the tuned model to determine the appropriate laser parameters and incidence angle to perform a cut that produces a feasible profile.

In one embodiment, the method includes: (STEP 1) acquire a profile (e.g., 3D image) of the crater with an imaging system; (STEP 2) label an obstacle boundary profile from the 2D slide images (obtained from the 3D scanner) to be achieved after laser ablation. In some embodiments, this can be a user defined obstacle boundary or automatically determined through segmentation in the biomedical image. (STEP 3) combine multiple 2D labelled boundaries to create a final 3D obstacle boundary profile. (STEP 4) convert the obstacle boundary profile to a Euclidean Distance Transform (EDT). As detailed herein, EDT is a method to quantify the distance between a query 3D point to the closest point at the obstacle boundary. EDT is used to measure the level of the collision for a 3D point (e.g., the one closer to the boundary is assigned a smaller EDT value because it is closer to the obstacle boundary). (STEP 5) determine the laser parameters that will achieve the desired cut within the obstacle boundary. The laser parameters are determined by solving the optimization problem detailed herein. The optimal laser incident angle is determined that can minimize the sum of obstacle costs (e.g., maximize the Euclidean Distance Transform metric between the predicted resulting surface profile and the obstacle boundary profile. This indicates that the resulting surface profile is far away from the obstacle boundary, which is located at a "safe region." In some embodiments, a mapping function converts the EDT metric to the obstacle cost, thus the optimization becomes a minimization problem instead of maximization. In some embodiments, a piecewise mapping function maps an EDT metric to an obstacle cost. In other words, given a 3D obstacle boundary with the associated Euclidean distance transforms, an arbitrary 3D position with a value referred as "obstacle cost" can be assigned as a way to measure the level of collision. This minimization can be achieved in some embodiments with the projected gradient method, or any suitable gradient-based constrained optimization method. (STEP 6) perform the ablation with the laser parameters determined. The results of the method disclosed herein finds the laser incident angle that results in the desired geometry of the post-ablation surface. In other words, the method determines an optimal laser incident vector to create a post-ablation profile that is inside the safe tissue region.

In some embodiments, the methods disclosed herein are utilized with conducting surgical simulation with different 3D sensor guided robotic laser platforms, such as stereovision, RGB-D camera and optical coherence tomography (OCT).

4. METHODS AND SYSTEMS

Embodiments of the present disclosure include a method comprising ablating a substrate with a laser at an orientation to create a cavity in the substrate, scanning the cavity, and creating a three-dimensional surface for the cavity. The method further includes storing the three-dimensional surface in a dataset. The dataset includes a laser projected distance as an independent variable and a depth of cut as a dependent variable. The method further includes fitting parameters of a gaussian-based model for the laser and the substrate based on the dataset.

In some embodiments, the orientation is a first orientation, the cavity is a first cavity, the three-dimension surface is a first three-dimensional surface, and wherein the method further includes: ablating the substrate with the laser at a second orientation to create a second cavity in the substrate; scanning the second cavity; creating a second three-dimensional surface of the second cavity; and storing the second three-dimensional surface in the dataset. In other words, the model fitting can be conducted for a single cavity or a plurality of a cavities.

In some embodiments, the substrate is a biological tissue. In some embodiments, the substrate is a tissue phantom. In some embodiments, the substrate is human tissue.

In some embodiments, scanning the cavity is with optical coherence tomography or micro computed tomography. In some embodiments, the method further includes creating a sequence of cross-sectional images of the cavity. In some embodiments, the sequence of cross-sectional images is filtered, segmented, and concatenated to create the three-dimensional surface for the cavity.

In some embodiments, the method further includes predicting a post-ablation surface using the gaussian-based model. In some embodiments, predicting the post-ablation surface includes providing a pre-ablation profile and a set laser orientation. In some embodiments, the method further includes projecting a point on the pre-ablation surface to a laser reference plane and calculating a projected distance to a laser center on the gaussian-based model.

In some embodiments, the method further includes determining a predicted depth of cut based on the projected distance to the laser center. In some embodiments, the method further includes collecting predicted depth of cuts for all points on the pre-ablation surface to generate the predicted post-ablation surface.

As described further herein, in some embodiments, a method comprising providing a pre-ablation surface; labeling a three-dimensional obstacle boundary that separates material to be remove by a laser and material to remain; and determining an orientation of the laser that results in a predicted post-ablation surface that does not intersect the three-dimension obstacle boundary.

In some embodiments, the method further includes predicting a plurality of post-ablation surfaces for a plurality of orientations of the laser. In some embodiments, predicting the plurality of post-ablation surface utilizes a gaussian-based model for the laser.

In some embodiments, the method further includes generating a Euclidean distance transform metric for each of the plurality of post-ablation surfaces. In some embodiments, the Euclidean distance transform metric is a measurement of a distance between a query point on the post-ablation surface to the closest point on the three-dimensional obstacle boundary. In some embodiments, a raw distance value from the Euclidean distance transform metric is post-processed to an oriented distance value with a negative value if the query point crosses the three-dimensional obstacle boundary. In other words, if a new point is inside the obstacle boundary (e.g., in a safe region), the oriented distance value should be positive, and if a new point is outside the obstacle boundary (e.g., in an overcutting non-safe region), the oriented distance value should be negative.

In some embodiments, the Euclidean distance transform metric is converted to an obstacle cost. In some embodiments, the obstacle cost is minimized with a gradient-based constrained optimization method.

In some embodiments, determining the orientation of the laser that results in the predicted post-ablation surface that does not intersect the three-dimension obstacle boundary includes maximizing a Euclidean distance transform metric between the predicted post-ablation surface and the three-dimensional obstacle boundary.

In some embodiments, the method further includes moving the laser to the orientation and energizing the laser. In some embodiments, the pre-ablation surface is tissue, the three-dimensional obstacle boundary separates tissue to be remove by the laser and tissue to remain; and wherein the laser is energized for laser-tissue resection.

The systems and methods described herein can be implemented in hardware, software, firmware, or combinations of hardware, software and/or firmware. In some examples, the systems and methods described in this specification may be implemented using a non-transitory computer readable medium storing computer executable instructions that when executed by one or more processors of a computer cause the computer to perform operations. Computer readable media suitable for implementing the systems and methods described in this specification include non-transitory computer-readable media, such as disk memory devices, chip memory devices, programmable logic devices, random access memory (RAM), read only memory (ROM), optical read/write memory, cache memory, magnetic read/write memory, flash memory, and application-specific integrated circuits. In addition, a computer readable medium that implements a system or method described in this specification may be located on a single device or computing platform or may be distributed across multiple devices or computing platforms.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

5. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

The data-driven method is validated using the Micro-CT data. 3D cavity point cloud data is collected from four incident angles with 10 repeated measurements. This formulates a dataset for the estimation of Gaussian function parameters $L_G$ and $\sigma_G$. The Gaussian function fitting is a non-linear curve fitting problem (e.g., least-squares minimization) and in some embodiments MATLAB "lsqcurvefit" optimization toolbox is used to find the fitted parameters. For the specified tissue material and laser parameters, in one embodiment, $L_G=1.4376$ and $\sigma_G=0.6486$ were obtained. The model re-projected Room-mean-square error is 0.1468 and this contributes to 10.2% of the $L_G$. This demonstrates the laser can generate a maximum depth of cut with around 1.44 mm at the ablation center. For generality of the problem, in some embodiments, a look-up table of laser-tissue models and parameters are provided, which can be used directly in robotic surgery.

Example 1

Validating the Analytical Gradient: Test 1 (Example 1) aims to validate the analytical gradient $\nabla q(\theta)$ by making a hypothesis that the update of the orientation can follow the EDT gradient vectors $\nabla\Phi(q(\theta))$. The $\nabla\Phi(q(\theta))$ refers to a vector direction with higher EDT values with respect to a surface position $q(\theta)$, which indicates a lower collision cost. For example, if given a vector $\nabla\Phi(q(\theta))>0$ and using the gradient ascent $\theta^{k+1}=\theta^k+\alpha*\nabla\theta\Phi(q(\theta^k))$ as the update rule, that results in EQN. 14.

$$\Phi^{k+1} = \Phi^k + \frac{(\theta^{k+1} - \theta^k)^2}{\alpha} + \Phi^k \geq \Phi^k \quad [14]$$

This indicates that if the angle is updated by the gradient ascent direction, the EDT value can increase and the ablated contour can maximize the distance to the obstacle boundary (minimize cost). Thus, the gradient ascent with $\nabla\Phi(\theta)$ is equal to the gradient descent with $\nabla C(\theta)$, because $\nabla C(\theta)$ is negative when the EDT value is smaller than the collision threshold. For brevity, the goal of using $\nabla\Phi(\cdot)$ with the gradient ascent rule is used to validate the feasibility of the analytical gradient.

For the simulated experiments, a "point robot" is defined for a surface position $q_i$ which follows the kinematic system in EQN. 4. The "point robot" refers to the change of movement of a surface position after a single laser incidence. The validation of the analytical gradient $\nabla q(\theta)$ can be achieved by observing the movement of the point robot.

Figure 9B:
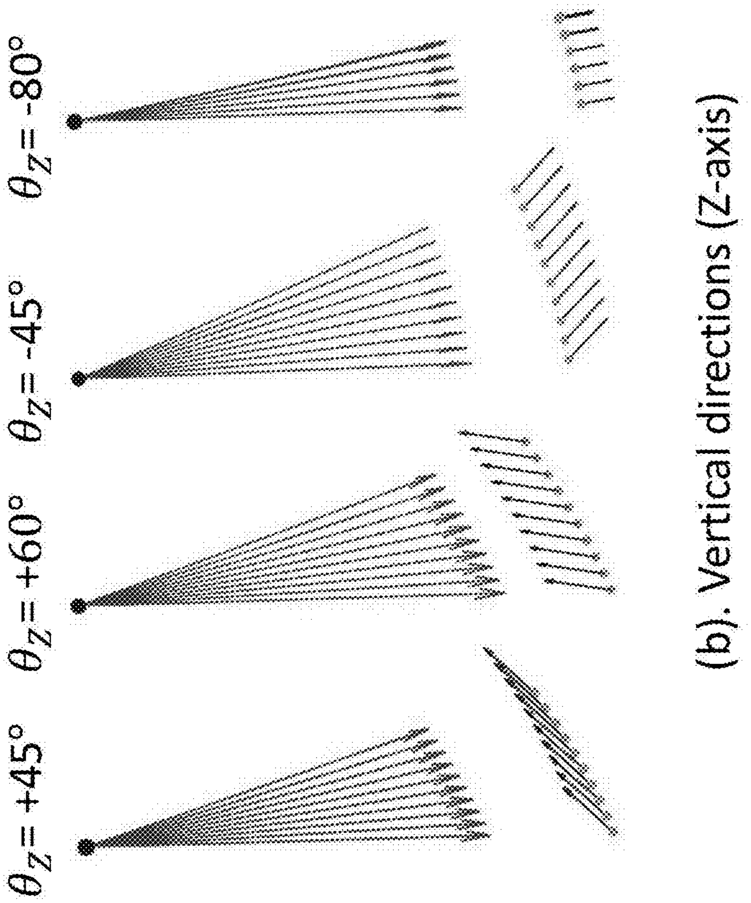
FIGS. 9A-B illustrate Test 1 (Example 1) orientation planning in 3D.

First, a 2D test is conducted to show that the 1-DOF orientation angle update can be guided by a reference direction. FIG. 8A illustrates that the incident orientation is guided by a fixed reference direction (left or right). For the 3D analysis, the orientation planning follows the gradient ascent update rule and is guided by the arbitrary 3-DOF reference vectors defined as $v_R=v_H+v_G$. This vector is generated by setting the rotation angles in [−180°, 180°] (horizontal) and [−80°, 80°] (vertical). It is noted that one of the rotation angles is repeated and thus not used to create the sample vectors. For each reference vector, an incident orientation controls the point robot to generate a trajectory. FIG. 9 illustrates the examples of controlling the angles to follow the reference trajectories.

Figure 9A:
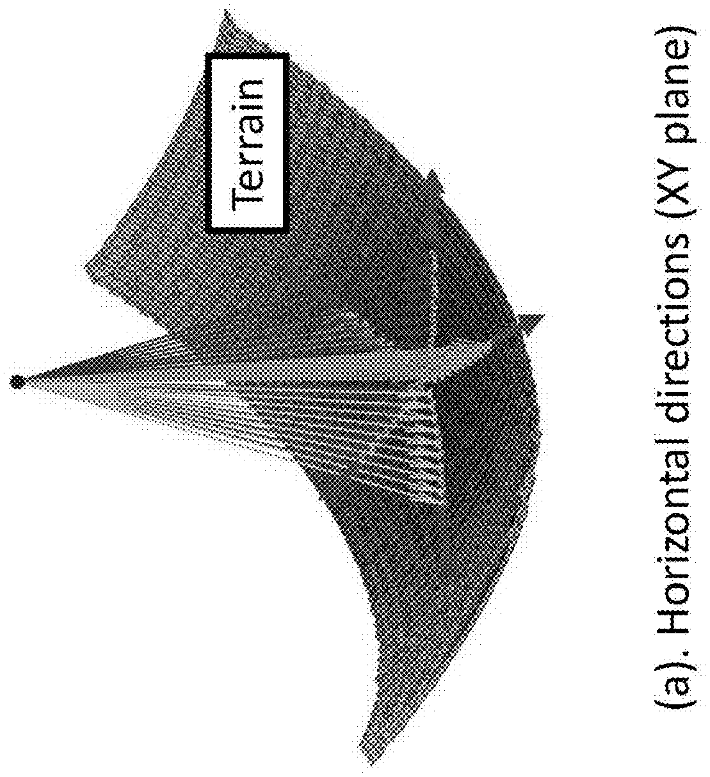

To validate the method, the orientation error is used to measure the difference between the reference vector and the point vector defined as $v_k=q_{k+1}-q_k$. As the point trajectory is located at a fixed surface terrain, as shown in FIG. 9A, only the vector offset in XY plane (e.g., horizontal direction) needs to be considered. This is because the point robot cannot be controlled to a new position guided by the vertical direction. The orientation error distribution is depicted in FIG. 11A. These results indicate that given a reference vector field in 3D, the point robot can be guided to follow these directions. The analytical gradient of $\nabla q(\theta)$ can correctly be applied to control the orientation angle guided by the EDT field.

Example 2

Sample Points Validation: Instead of using a fixed reference vector, Test 2 (Example 2) validates the hypothesis that the point robots can follow a vector field created by an arbitrary obstacle boundary. It is noted that the gradient descent rule with an analytical gradient $\nabla f(\theta, q_i)$ is used in this example. The laser-tissue model parameters are estimated by the Micro-CT data, as discussed herein. Six Gaussian-shape obstacle boundaries are defined by setting various variance parameters and formulate the obstacle vector fields in simulation. For each obstacle terrain, a surface grid is defined with different initial positions by setting nine random incident angles. In this example, each surface grid contains 49 point robots and this ensures that each sample point is located at an arbitrary starting position. The goal is to control each point robot to move to a low-cost position and keep adequate distance to the obstacle boundary. FIG. 10B shows an example of the point robot trajectories and all the points can successfully be "attracted" to the inner obstacle boundary.

Figure 11B:
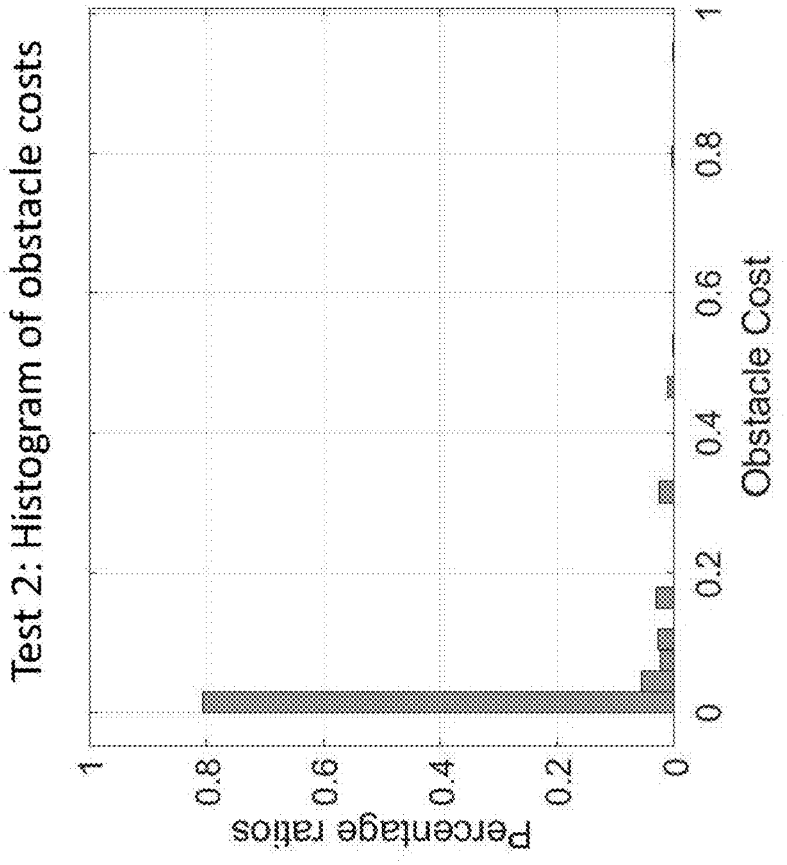
FIGS. 11A-B are error histograms of Example 1 and Example 2.
Figure 11A:
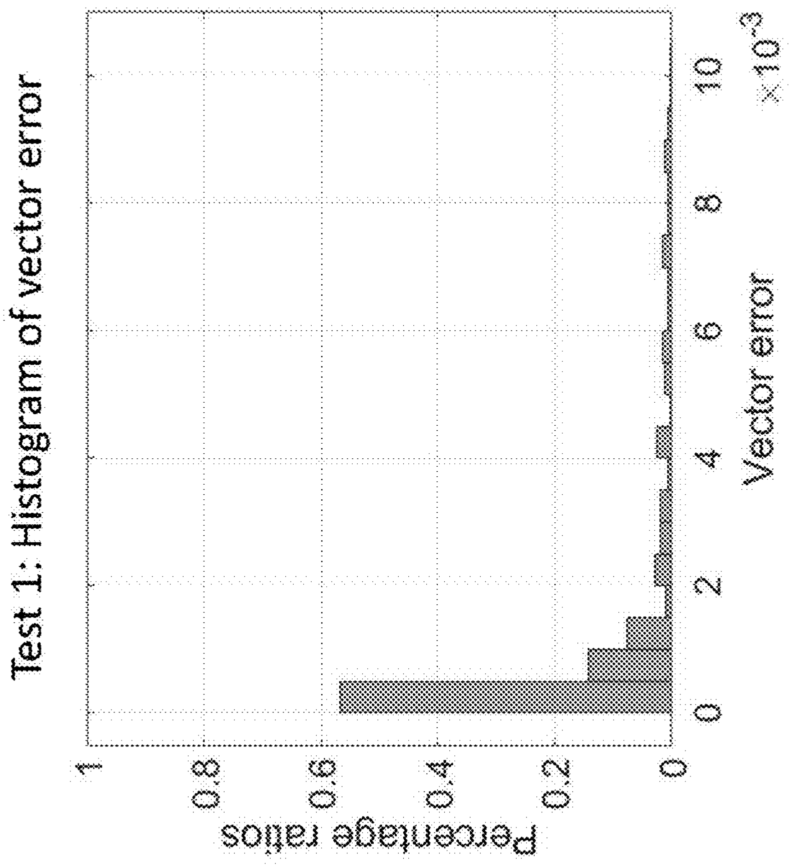

FIG. 11B illustrates the error histogram of the final obstacle costs at the last step (after optimization). The majority of the point robots can be positioned with low obstacle costs (≤0.5) based on a collision threshold as 0.6. This demonstrates the feasibility of calculating the optimal orientation angle for a single point robot movement with arbitrary initial conditions and boundary terrains.

Example 3

Surface Validation: Test 3 (Example 3) validates the orientation planning method by using the gradient information from all the point robots at the surface, instead of an individual one. The experimental conditions in Example 2 are applied to this example. The Projected gradient descent and the Data selection methods are tested with the analytical gradient $\nabla f(\theta \cdot q_i)$.

Figure 12A:
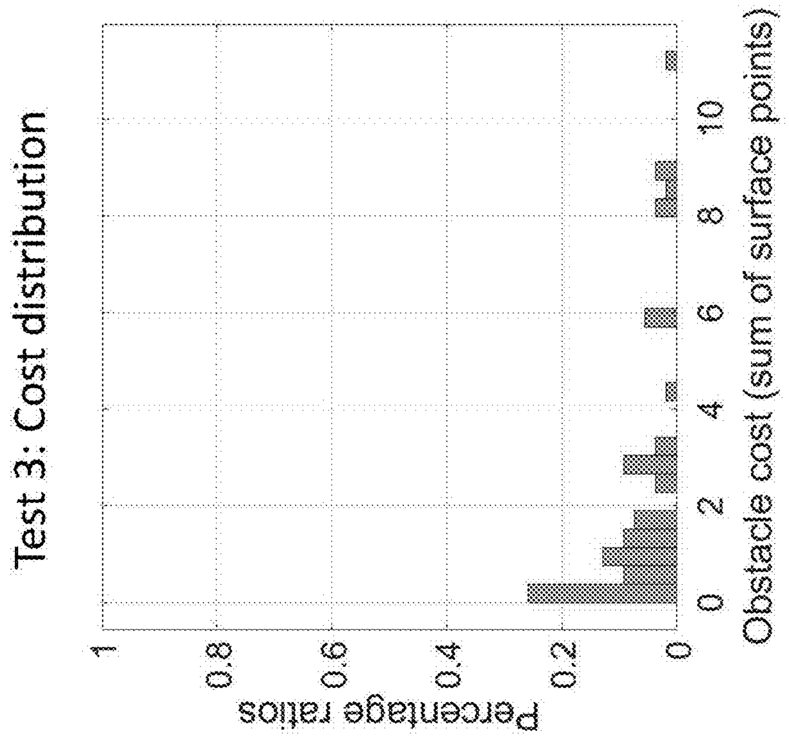
FIGS. 12A-B show results analysis for Example 3.
Figure 12B:
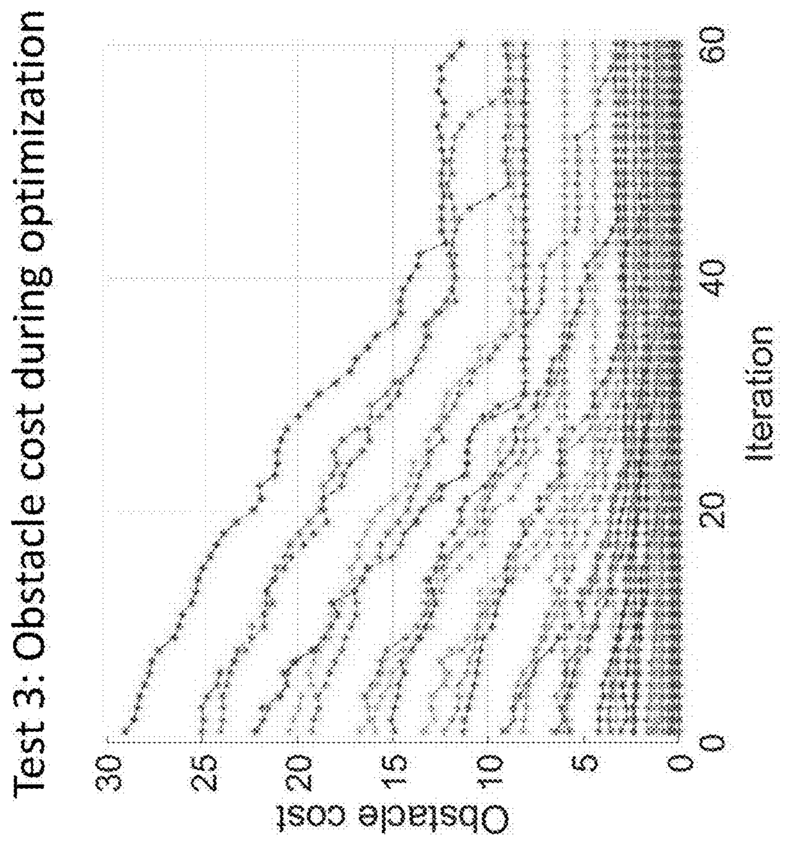

The obstacle costs of all the point robots are collected for evaluation. FIG. 12A illustrates the cost distribution of the last step (after optimization). It shows that a high ratio of the sample surfaces can be controlled to the low-cost positions. FIG. 12B represents the trend of the obstacle costs for all the experimental conditions. Most cases can show the reduction of obstacle cost after the planning. For some surfaces initially localized at the correct positions, the obstacle cost has already remained at a low-cost level. It is noted that for cases where the contour of the Gaussian shape boundary is smaller than the sample surface, the final obstacle cost cannot reach to zero or a very small value.

FIGS. 10C-10F depict the 3D cavities before and after the optimization. The ablated contours can successfully move to a "safe" position inside the obstacle boundary after the planning. These results demonstrate the efficacy of the orientation planner in creating an ablated profile inside the obstacle boundary.

It is understood that the foregoing detailed description and accompanying examples are merely illustrative and are not to be taken as limitations upon the scope of the disclosure, which is defined solely by the appended claims and their equivalents.

Various changes and modifications to the disclosed embodiments will be apparent to those skilled in the art.

What is claimed is:

1. A method comprising:

ablating a substrate with a laser at an orientation to create a cavity in the substrate;

scanning the cavity;

creating a three-dimensional surface for the cavity;

storing the three-dimensional surface in a dataset, wherein the dataset includes a laser projected distance as an independent variable and a depth of cut as a dependent variable;

fitting parameters of a gaussian-based model for the laser and the substrate based on the dataset;

predicting a post-ablation surface using the gaussian-based model based on a pre-ablation profile and a set laser orientation, wherein predicting the post-ablation surface includes projecting a point on the pre-ablation surface to a laser reference plane; and calculating a projected distance to a laser center on the gaussian-based model.

2. The method of claim 1, wherein the orientation is a first orientation, the cavity is a first cavity, the three-dimension surface is a first three-dimensional surface, and wherein the method further includes:

ablating the substrate with the laser at a second orientation to create a second cavity in the substrate;

scanning the second cavity;

creating a second three-dimensional surface of the second cavity; and storing the second three-dimensional surface in the dataset.

3. The method of claim 1, wherein the substrate is a biological tissue.

4. The method of claim 1, wherein scanning the cavity is with optical coherence tomography or micro computed tomography.

5. The method of claim 1, wherein the method further includes creating a sequence of cross-sectional images of the cavity.

6. The method of claim 5, wherein the sequence of cross-sectional images is filtered, segmented, and concatenated to create the three-dimensional surface for the cavity.

7. The method of claim 1, wherein predicting the post-ablation surface further includes determining a predicted depth of cut based on the projected distance to the laser center.

8. The method of claim 7, wherein predicting the post-ablation surface further includes collecting predicted depth of cuts for all points on the pre-ablation surface to generate the predicted post-ablation surface.

9. A method comprising:

providing a pre-ablation surface;

labeling a three-dimensional obstacle boundary that separates material to be removed by a laser and material to remain;

predicting, using a gaussian-based model for the laser, a plurality of post-ablation surfaces for a plurality of orientations of the laser relative to the pre-ablation surface;

generating a Euclidean distance transform metric for each of the plurality of post-ablation surfaces; wherein the Euclidean distance transform metric is a measurement of a distance between a query point on the post-ablation surface to the closest point on the three-dimensional obstacle boundary;

determining an optimum orientation of the laser from the plurality of orientations of the laser that results in a predicted post-ablation surface that does not intersect the three-dimensional obstacle boundary and maximizes the Euclidean distance transform metric between the predicted post-ablation surface and the three-dimensional obstacle boundary;

moving the laser to the optimum orientation; and energizing the laser while positioned at the optimum orientation.

10. The method of claim 9, wherein a raw distance value from the Euclidean distance transform metric is post-processed to an oriented distance value with a negative value if the query point crosses the three-dimensional obstacle boundary.

11. The method of claim 9, wherein the Euclidean distance transform metric is converted to an obstacle cost.

12. The method of claim 11, wherein the obstacle cost is minimized with a gradient-based constrained optimization method.

13. The method of claim 9, wherein the pre-ablation surface is tissue, the three-dimensional obstacle boundary separates tissue to be removed by the laser and tissue to remain; and wherein the laser is energized for laser-tissue resection.

* * * * *